US012687486B2

(12) United States Patent
Fukutake et al.

(10) Patent No.: US 12,687,486 B2
(45) Date of Patent: Jul. 21, 2026

(54) IMAGE PROCESSING METHOD, IMAGE PROCESSING DEVICE, AND PROGRAM

(71) Applicants: NIKON CORPORATION, Tokyo (JP); UNIVERSITY OF TSUKUBA, Tsukuba (JP)

(72) Inventors: Naoki Fukutake, Tokyo (JP); Yoshiaki Yasuno, Tsukuba (JP); Shuichi Makita, Tsukuba (JP)

(73) Assignees: NIKON CORPORATION;, Tokyo (JP); UNIVERSITY OF TSUKUBA, Tsukuba (JP)

( * ) Notice: Subject to any disclaimer, the term of this patent is extended or adjusted under 35 U.S.C. 154(b) by 123 days.

(21) Appl. No.: 18/892,126

(22) Filed: Sep. 20, 2024

(65) Prior Publication Data

US 2025/0110040 A1 Apr. 3, 2025

Related U.S. Application Data

(63) Continuation of application No. PCT/JP2023/009452, filed on Mar. 10, 2023.

(30) Foreign Application Priority Data

Mar. 24, 2022 (JP) ................................. 2022-048770

(51) Int. Cl.
G01N 21/17 (2006.01)
A61B 3/10 (2006.01)
G06T 11/00 (2006.01)

(52) U.S. Cl.
CPC ............... *G01N 21/17* (2013.01); *A61B 3/10* (2013.01); *G06T 11/00* (2013.01)

(58) Field of Classification Search
CPC ........ G01N 21/17; A61B 3/10; A61B 3/0025; A61B 3/102; G06T 11/00

(Continued)

(56) References Cited

U.S. PATENT DOCUMENTS 7,236,251 B2 * 6/2007 Takaoka ............. G02B 21/0072
356/497
9,408,531 B2 * 8/2016 Okada ................... A61B 3/117
(Continued)

FOREIGN PATENT DOCUMENTS

JP 2016-041222 A 3/2016

OTHER PUBLICATIONS

Japanese Office Action for JP Patent Appl. No. 2024-510010 dated Aug. 19, 2025.

*Primary Examiner* — Isiaka O Akanbi
(74) *Attorney, Agent, or Firm* — Foley & Lardner LLP

(57) ABSTRACT

An image processing device illuminates light from a light source through an optical system with a first numerical aperture onto an examined eye, transmits signal light returning from the examined eye through an optical system with a second numerical aperture, and divides a reference light from the light from the light source. The image processing device detects interference light between the signal light and the reference light, and acquires information representing the obtained interference light. The image processing device performs a first process of projecting the information representing the interference light onto a four-dimensional frequency aperture formed by the optical system with the first numerical aperture and the optical system with the second numerical aperture, in a four-dimensional space of frequencies of the light source and frequencies of light from the examined eye according to the signal light, and a second process of projecting the projected information into three-dimensional space.

12 Claims, 11 Drawing Sheets

(58) Field of Classification Search
USPC .......................... 356/432, 479, 490–495, 497
See application file for complete search history.

(56)                    References Cited

U.S. PATENT DOCUMENTS

| | | | |
|---|---|---|---|
| 10,238,281 B2 | 3/2019 | Isogai et al. | |
| 2007/0229801 A1* | 10/2007 | Teamney | G02B 23/243 |
| | | | 356/73 |
| 2014/0115022 A1* | 4/2014 | Yasuno | G01B 9/02088 |
| | | | 708/204 |
| 2017/0105618 A1* | 4/2017 | Schmoll | G01B 9/02044 |
| 2017/0199116 A1* | 7/2017 | Yasuno | G01N 21/21 |
| 2018/0242840 A1* | 8/2018 | Copland | A61B 3/1005 |
| 2018/0259316 A1* | 9/2018 | Tumlinson | G01B 9/02091 |
| 2018/0303339 A1* | 10/2018 | Moriguchi | A61B 3/102 |

* cited by examiner

FIG.2

IMAGE PROCESSING METHOD, IMAGE PROCESSING DEVICE, AND PROGRAM

CROSS-REFERENCE TO RELATED APPLICATIONS

This application is a continuation application of International Application No. PCT/JP2023/009452, filed Mar. 10, 2023, the disclosure of which is incorporated herein by reference in its entirety. Further, this application claims priority from Japanese Patent Application No. 2022-048770, filed Mar. 24, 2022, the disclosure of which is incorporated herein by reference in its entirety.

TECHNICAL FIELD

The technology of the present disclosure relates to an image processing method, an ophthalmological device and a program.

BACKGROUND ART

Optical coherence tomography uses light reflected from different layers of the fundus of an eye that is being examined to enable observation of structures of the examined eye. Optical coherence tomography (OCT) may provide two-dimensional tomography images and three-dimensional images, with one dimension being a depth direction. For example, technologies are known that use optical coherence tomography to generate data relating to the structure of an examined eye (U.S. Pat. No. 10,238,281).

SUMMARY OF INVENTION

A first aspect of the technology of the present disclosure is an image processing method to be carried out by a processor at an image processing device, the image processing method including: acquiring information representing interference light that is obtained by illuminating light from a light source through an optical system with a first numerical aperture onto an illuminated side object, transmitting signal light returning from the illuminated side object in response to the illuminated light through an optical system with a second numerical aperture, dividing a reference light from the light from the light source, and detecting the interference light between the signal light and the reference light; and performing processing including: a first process of projecting the information representing the interference light onto a four-dimensional frequency aperture formed by the optical system with the first numerical aperture and the optical system with the second numerical aperture in a four-dimensional space of frequencies of the light source and frequencies of light in three dimensions representing the illuminated side object, and a second process of projecting the information projected by the first process into three-dimensional space.

A second aspect of the technology of the present disclosure is an image processing device including memory and a processor, the processor being configured to: acquire information representing interference light that is obtained by illuminating light from a light source through an optical system with a first numerical aperture onto an illuminated side object, transmitting signal light returning from the illuminated side object in response to the illuminated light through an optical system with a second numerical aperture, dividing a reference light from the light from the light source, and detecting the interference light between the signal light and the reference light; and perform processing including: a first process of projecting the information representing the interference light onto a four-dimensional frequency aperture formed by the optical system with the first numerical aperture and the optical system with the second numerical aperture in a four-dimensional space of frequencies of the light source and frequencies of light in three dimensions representing the illuminated side object, and a second process of projecting the information projected by the first process into three-dimensional space.

A third aspect of the technology of the present disclosure is a non-transitory storage medium storing a program for causing a computer to execute processing including: acquiring information representing interference light that is obtained by illuminating light from a light source through an optical system with a first numerical aperture onto an examined eye, transmitting signal light returning from the examined eye in response to the illuminated light through an optical system with a second numerical aperture, dividing a reference light from the light from the light source, and detecting the interference light between the signal light and the reference light; and performing processing including: a first process of projecting the information representing the interference light onto a four-dimensional frequency aperture formed by the optical system with the first numerical aperture and the optical system with the second numerical aperture in a four-dimensional space of frequencies of the light source and frequencies of light from the examined eye, and a second process of projecting the information projected by the first process into three-dimensional space.

BRIEF DESCRIPTION OF DRAWINGS

FIG. 2 is a schematic structural diagram of an ophthalmological device according to the exemplary embodiment.

DETAILED DESCRIPTION

Below, an ophthalmology system 100 according to an exemplary embodiment of the present invention is described with reference to the drawings.

Figure 1:
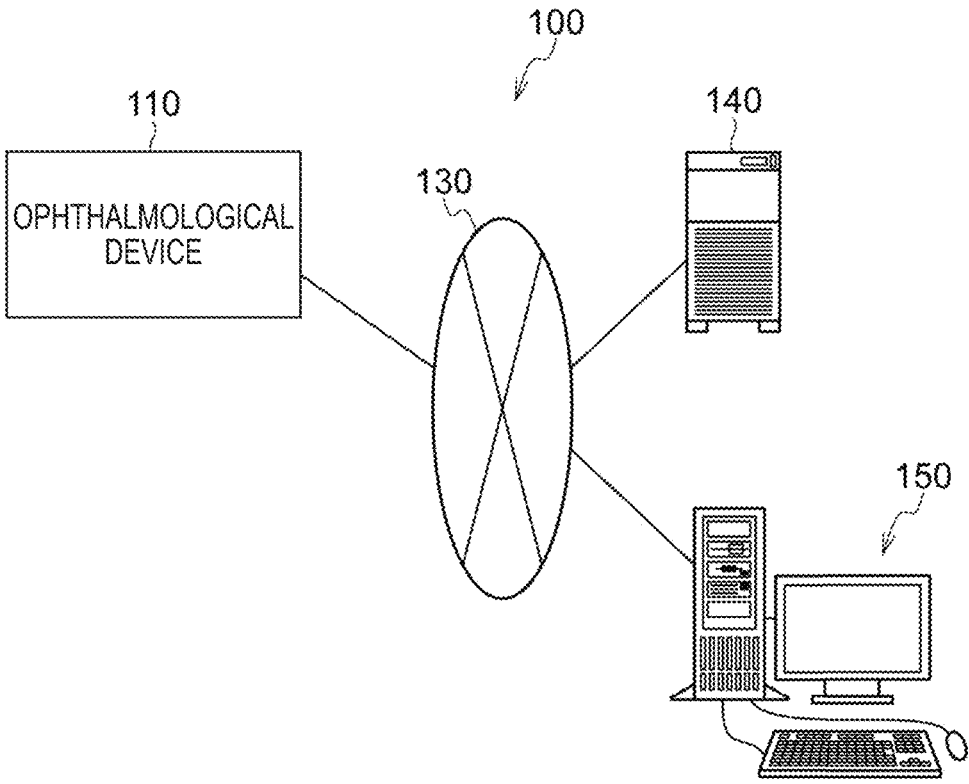
FIG. 1 is a schematic structural diagram of an ophthalmology system according to an exemplary embodiment.

FIG. 1 shows schematic structures of the ophthalmology system 100. As shown in FIG. 1, the ophthalmology system 100 includes an ophthalmological device 110, a server device (below referred to as "the server") 140, and a display device (below referred to as "the viewer") 150. The ophthalmological device 110 acquires fundus images. The server 140 memorizes plural fundus images obtained by imaging funduses of plural patients with the ophthalmological device 110 and eye axial lengths measured by an eye axial length measurement device, which is not shown in the drawings, in association with patient IDs. The viewer 150 displays fundus images, analysis results and the like acquired by the server 140.

In the present exemplary embodiment, a situation is described in which an examined eye is an example of an illuminated side object of the technology of the present disclosure. The ophthalmological device 110 is an example of an ophthalmological device of the technology of the present disclosure. The ophthalmological device is also an example of an image processing device of the technology of the present disclosure.

The ophthalmological device 110, the server 140 and the viewer 150 are connected to one another via a network 130. The network 130 is an arbitrary network such as a LAN, a WAN, the Internet, a wide area Ethernet or the like. For example, when the ophthalmology system 100 is constituted in a medical facility such as a single hospital or the like, a LAN may be employed for the network 130.

The viewer 150 is a client of a client-server system. A multiplicity of the viewer 150 are connected via the network. To assure system redundancy, a multiplicity of the server 140 may be connected via the network. If the ophthalmological device 110 is equipped with image processing functions and image inspection functions for the viewer 150, the ophthalmological device 110 may implement acquisition of fundus images, image processing and image inspection in a stand-alone state. If the server 140 is equipped with image inspection functions for the viewer 150, a configuration of the ophthalmological device 110 and the server 140 may implement acquisition of fundus images, image processing and image inspection.

A diagnosis assistance device that uses another ophthalmological device (examination equipment for field of vision measurement, intraocular pressure measurement or the like), artificial intelligence (AI) or the like to conduct image analysis may also be connected to the ophthalmological device 110, the server 140 and the viewer 150 via the network 130.

Now, structures of the ophthalmological device 110 are described with reference to FIG. 2.

For convenience of description, a scanning laser ophthalmoscope is referred to as an "SLO", and optical coherence tomography is referred to as "OCT".

When the ophthalmological device 110 is disposed on a horizontal surface, a horizontal direction is referred to as "the X direction", a direction perpendicular to the horizontal surface is referred to as "the Y direction", and a direction linking the center of a pupil at an anterior portion of an examined eye 12 with the center of the eyeball is referred to as "the Z direction". Thus, the X direction, Y direction and Z direction are mutually perpendicular.

The ophthalmological device 110 includes an imaging device 14 and a control device 16. The imaging device 14 is equipped with an SLO unit 18 and an OCT unit 20. The imaging device 14 acquires fundus images of the examined eye 12. Below, a two-dimensional fundus image acquired by the SLO unit 18 is referred to as an SLO image. A tomography image of the retina, a front elevation image (an en-face image) or the like that is created on the basis of OCT data acquired by the OCT unit 20 may be referred to as an OCT image.

The control device 16 is provided with a computer including a central processing unit (CPU) 16A, random access memory (RAM) 16B, read-only memory (ROM) 16C and an input/output (I/O) port 16D.

The control device 16 is further provided with an entry/display device 16E connected to the CPU 16A via the I/O port 16D. The entry/display device 16E has a graphical user interface that displays images of the examined eye 12 and accepts various instructions from a user. A touch panel display or the like may be employed as the graphical user interface.

The control device 16 is further provided with an image processing device 17 connected to the I/O port 16D. The image processing device 17 generates images of the examined eye 12 on the basis of data obtained by the imaging device 14. The control device 16 is connected to the network 130 via a communications interface 16F. The image processing device 17 is equipped with memory 17M, which is a non-volatile memory device capable of memorizing an image processing program, which is described below.

As described above, in FIG. 2 the control device 16 of the ophthalmological device 110 is provided with the entry/display device 16E, but the technology of the present disclosure is not limited thus. For example, rather than the control device 16 of the ophthalmological device 110 being provided with the entry/display device 16E, a separate entry/display device that is physically independent of the ophthalmological device 110 may be provided. In this situation, the display device may be equipped with an image processing processor unit, and the image processing processor unit may display SLO images and the like on the basis of image signals outputted from the ophthalmological device 110.

The imaging device 14 operates under the control of the CPU 16A of the control device 16. The imaging device 14 includes an SLO unit 18, an imaging optical system 19 and the OCT unit 20. The imaging optical system 19 includes an optical scanner 22 and a wide-angle optical system 30.

The optical scanner 22 scans light emitted from the SLO unit 18 two-dimensionally in the X direction and the Y direction. It is sufficient that the optical scanner 22 is an optical component that is capable of deflecting light flux; for example, a polygon mirror, a galvano mirror or the like may be employed. Combinations of these components may be used.

The wide-angle optical system 30 combines light from the SLO unit 18 with light from the OCT unit 20.

The wide-angle optical system 30 may be a reflecting optical system using a concave mirror such as an elliptical mirror or the like, a refracting optical system using a wide-angle lens or the like, or a reflecting and refracting optical system combining a concave mirror with a lens or the like. When a wide-angle optical system using an elliptical mirror and a wide-angle lens or the like is employed, areas of the retina around the fundus may be imaged rather than just a central fundus area.

When a system including an elliptical mirror is employed, the system using an elliptical mirror may be configured as recited in International Publication No. WO2016/103484 or WO2016/103489. The respective disclosures of International Publication Nos. WO2016/103484 and WO2016/103489 are incorporated into the present specification by reference in their entirety.

Observation of a wide field of view (FOV) region 12A of the fundus is realized by the wide-angle optical system 30. The FOV region 12A represents a range that can be imaged by the imaging device 14. The FOV region 12A may be expressed as a viewing angle. A viewing angle in the present exemplary embodiment may be specified as an internal illumination angle and an external illumination angle. The external illumination angle is an illumination angle of light flux illuminated from the ophthalmological device 110 toward the examined eye 12 specified by reference to a pupil 27. The internal illumination angle is an illumination angle of light flux illuminated toward a fundus F specified by reference to an eyeball center O. The external illumination angle and internal illumination angle have a correspondence relationship. For example, an external illumination angle of 120° corresponds to an internal illumination angle of around 160°. In the present exemplary embodiment, the internal illumination angle is 200°.

An SLO fundus image that is obtained by imaging with an internal illumination angle of 160° or more as an imaging field of view is referred to as a UWF-SLO fundus image. "UWF" is an abbreviation of "ultra-wide field". A region extending beyond an equatorial region of the fundus of the examined eye 12 from the posterior pole area may be imaged by the wide-angle optical system 30 with the field of view (FOV) of the fundus that has an ultra-wide field angle.

The ophthalmological device 110 may image the region 12A with an internal illumination angle of 200°, with the eyeball center O of the examined eye 12 as the reference point. The internal illumination angle of 200° corresponds to an external illumination angle of 110° by reference to the pupil of the eyeball of the examined eye 12. In other words, the wide-angle optical system 30 illuminates laser light with the external illumination angle of 110° through the pupil and images the fundus region with the internal illumination angle of 200°.

Figure 2:
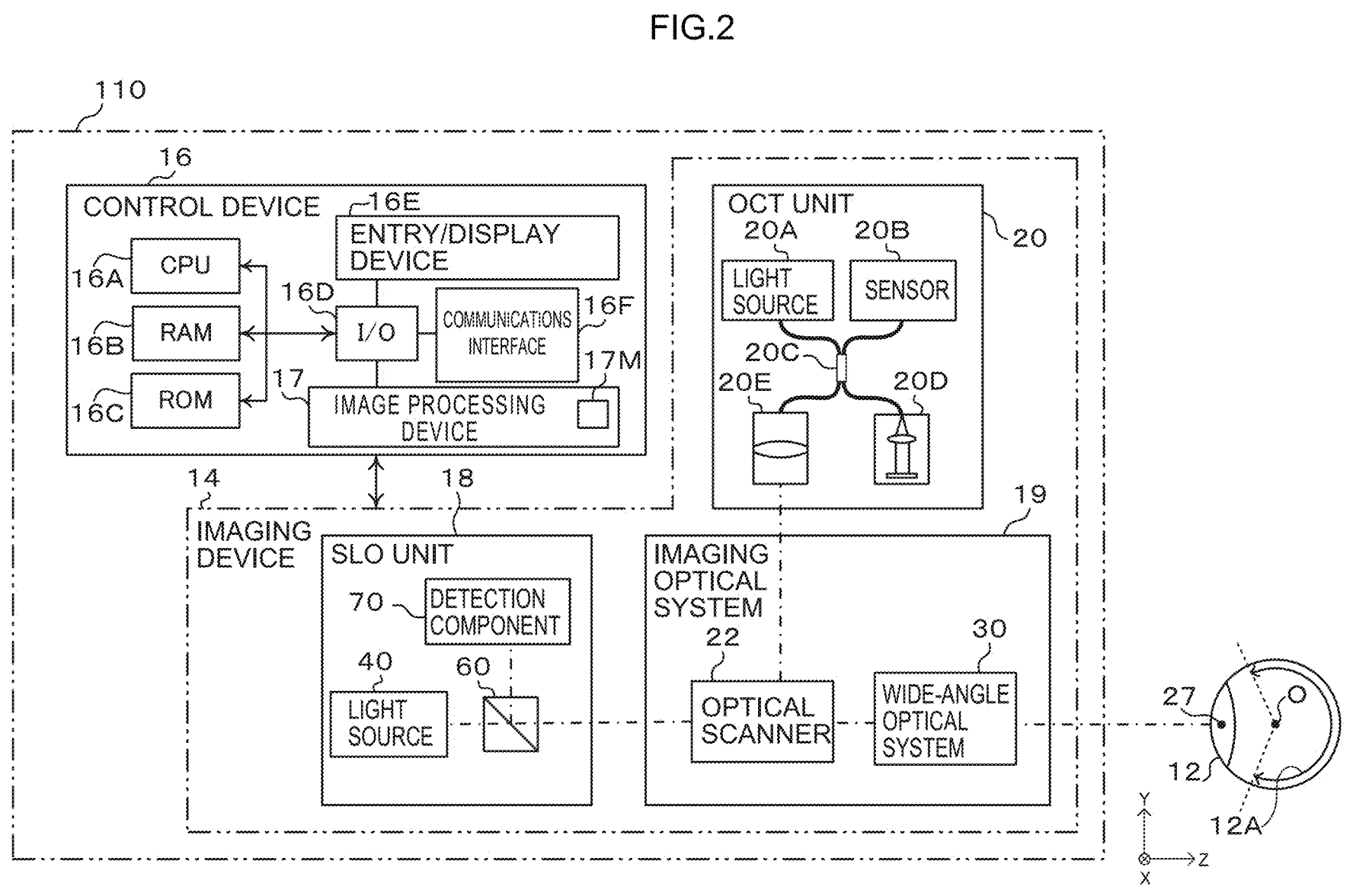

An SLO system is realized by the control device 16, SLO unit 18 and imaging optical system 19 shown in FIG. 2. Because the wide-angle optical system 30 is provided, the SLO system is capable of fundus imaging of the region 12A with the wide field of view.

The SLO unit 18 is provided with a light source 40 including a B (blue light) light source, a G (green light) light source, an R (red light) light source, and an IR (infrared radiation (for example, near-infrared light)) light source. Lights of the respective colors from the light source 40 are guided along the same optical path.

The SLO unit 18 is configured to be capable of switching a combination of light sources emitting laser lights or light sources emitting lights with different wavelengths between a mode that emits R light and G light, a mode that emits infrared light, and so forth. The technology of the present disclosure is not limited to the provision of four light sources—the B light source, G light source, R light source and IR light source. For example, the SLO unit 18 may be further provided with a light source for white light and may emit light in various modes such as a mode that omits G light, R light and B light, a mode that emits only white light, and so forth.

Light from the SLO unit 18 that enters the imaging optical system 19 is scanned in the X direction and the Y direction by the optical scanner 22. The scanned light passes through the wide-angle optical system 30 and the pupil 27 and is illuminated onto the fundus. Reflected light that is reflected by the fundus passes back through the wide-angle optical system 30 and the optical scanner 22 and enters the SLO unit 18.

The SLO unit 18 is provided with a beam splitter 60 that guides light from the posterior portion (the fundus) of the examined eye 12 to a detection component 70. The detection component 70 detects the light from the posterior portion (fundus) of the examined eye 12. The beam splitter 60 and the detection component 70 may be provided for each of the colors. For example, respective beam splitters for B light, G light, R light and IR light may be disposed on the optical axis, and detection elements for the corresponding colors may be disposed at downstream sides of the respective beam splitters. A beam splitter for B light that reflects the B light and transmits light other than B light is appropriate. Similarly, a beam splitter for G light that reflects the G light and transmits light other than G light, a beam splitter for R light that reflects the R light and transmits light other than R light, and a beam splitter for IR light that reflects the IR light are appropriate.

The image processing device 17 operates under the control of the CPU 16A. The image processing device 17 uses light that is incident on the SLO unit 18 via the wide-angle optical system 30 and the optical scanner 22 (reflected light that has been reflected by the fundus), that is, signals from the detection component 70 according to the light of each color, to generate a UWF-SLO image.

When the control device 16 controls the light source 40 for the respective colors so as to emit lights simultaneously and the fundus of the examined eye 12 is imaged simultaneously with the B light, G light and R light, a green fundus image, a red fundus image and a blue fundus image with mutually corresponding positions are obtained. An RGB color fundus image is obtained from the green fundus image, red fundus image and blue fundus image. When the control device 16 controls the light source 40 for the respective colors so as to emit lights simultaneously and the fundus of the examined eye 12 is imaged simultaneously with the G light and R light, a green fundus image and a red fundus image with mutually corresponding positions are obtained. An RG color fundus image is obtained from the green fundus image and red fundus image.

The region extending beyond the equatorial region of the fundus of the examined eye 12 from the posterior pole area may be imaged by the wide-angle optical system 30 with the field of view of the fundus that has an ultra-wide field angle.

An OCT system is realized by the control device 16, the OCT unit 20 and the imaging optical system 19 shown in FIG. 2. Because the wide-angle optical system 30 is provided, the OCT system is capable of OCT imaging of fundus periphery portions, similarly to the imaging of SLO fundus images described above. That is, OCT imaging of a region extending beyond the equatorial region of the fundus of the examined eye 12 from the posterior pole area is enabled by the wide-angle optical system 30 with the field of view (FOV) of the fundus that has an ultra-wide field angle. OCT data of fundus periphery portions may be acquired, and 3D structures of the fundus may be obtained by tomography and image processing of the OCT data.

Figure 3:
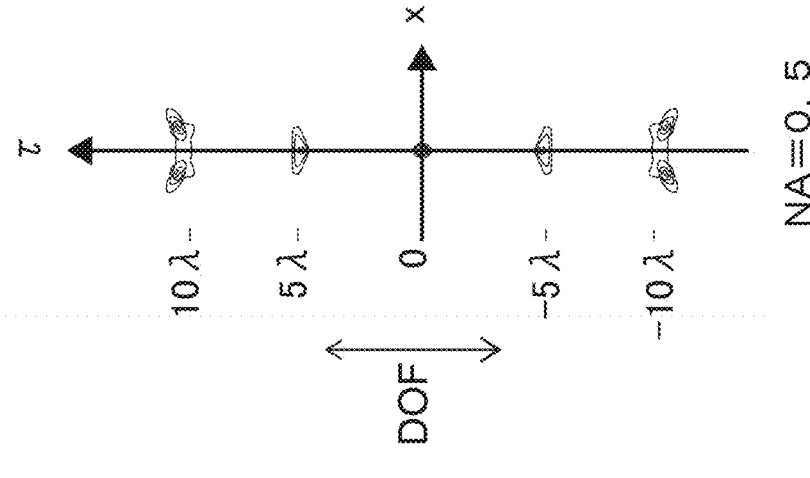
FIG. 3 is conceptual views of OCT images.
Figure 3:
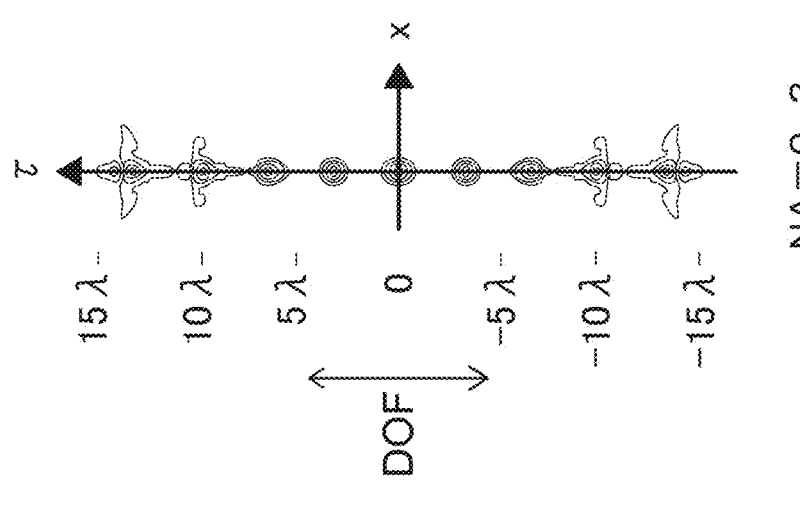
Figure 3:
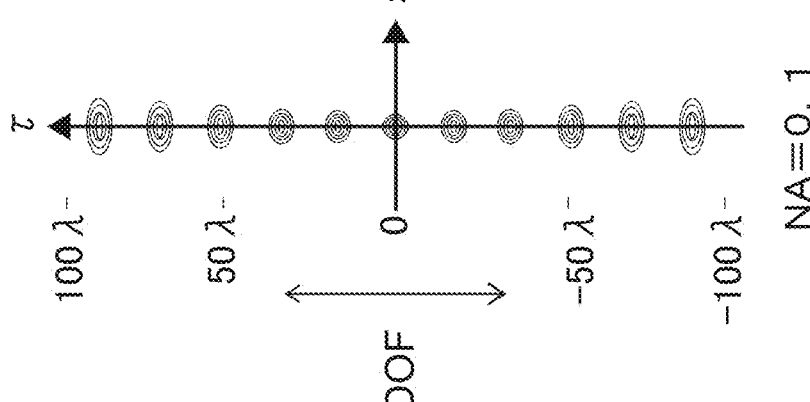

The OCT unit 20 includes a light source 20A, a sensor (detection component) 20B, a first light coupler 20C, a reference light optical system 20D, and an emission and detection optical system 20E including a second light coupler 200 (FIG. 3).

The light emitted from the light source 20A is split by the first light coupler 20C. One of the split lights serves as measurement light, passes through the emission and detection optical system 20E, and enters the imaging optical system 19. The measurement light passes through the wide-angle optical system 30 and the pupil 27 and is illuminated onto the fundus. The measurement light reflected by the fundus passes through the wide-angle optical system 30 and the optical scanner 22, is incident on the OCT unit 20, and is incident on the sensor 20B via the emission and detection optical system 20E and the first light coupler 20C. The other light split by the first light coupler 20C is incident on the reference light optical system 20D, returns as reference light, and is incident on the sensor 20B via the first light coupler 20C.

The lights entering the sensor 20B, which is to say the measurement light reflected from the fundus and the reference light, interfere and produce interference light. The interference light is sensed by the sensor 20B. The image processing device 17 operating under the control of the CPU 16 generates OCT data detected by the sensor 20B. Tomography images and OCT images may be generated on the basis of this OCT data.

The OCT unit 20 described above may scan a predetermined range (for example, a 6 mm×6 mm rectangular range) in a single cycle of OCT imaging. The predetermined range is not limited to 6 mm×6 mm but may be a square range of 12 mm×12 mm, 23 mm×23 mm or the like, may be a rectangular range of 14 mm×9 mm, 6 mm×3.5 mm or the like, and may be an arbitrary rectangular range. A circular range with a diameter of 6 mm, 12 mm, 23 mm or the like is also possible.

Because the wide-angle optical system 30 is employed, a scanning object of the ophthalmological device 110 may be the examined eye 12 over the internal illumination angle of 200°. That is, OCT imaging of the predetermined range is implemented by control of the optical scanner 22. The ophthalmological device 110 may generate OCT data by OCT imaging. Hence, the ophthalmological device 110 may generate an OCT image that is a fundus tomography image (a B-scan image), OCT volume data, or en-face images that are slices of the OCT volume data (front elevation images generated from the OCT volume data).

The OCT data (or image data of OCT images) is sent from the ophthalmological device 110 to the server 140 via the communications interface 16F and is memorized in a memory device.

This OCT system may acquire information in the depth direction of the fundus simultaneously. FIG. 3 shows examples of images of a dot (OCT images) arrayed along the optical axis that are simultaneously acquired by the OCT system using optical systems (for example, objective lenses) with different numerical apertures (below, "NA"). FIG. 3 shows examples of images of the dot arrayed along the optical axis in accordance with respective optical systems with NA=0.1, NA=0.3 and NA=0.5. In FIG. 3, depth direction axes, at the same position on the x axis, are measured in cτ, in which c represents luminous flux. In the drawings, cτ=τ; a unit system in which c=1 is employed below. A depth of focus of an optical system is indicated by DOF. As shown by the examples in FIG. 3, an image of a dot acquired by the OCT system becomes an imperfect image of the dot as a position in the depth direction of the fundus gets further from a focusing position (for example, the depth of focus) of the optical system. That is, as a position at which information relating to the fundus is acquired gets further from the focusing position of the imaging optical system 19 (for example, the depth of focus), the resolution progressively declines. Therefore, progressively further beyond the depth of focus, an imperfect image of the dot with blurring, distortion and the like is obtained. Information of the fundus at an outer side that is separated by a predetermined distance from the depth of focus (for example, around ten times) is partially lost. In usual image processing that is generally employed, completely restoring the lost information would be difficult. Technologies are available that apply processing such as deconvolution and refocusing to correct blurring and distortion of images outside the depth of focus, but because some information is lost at the time the image information is acquired, the correction is imperfect.

Imperfection of restoration of an OCT image by an OCT system is likely to be because information relating to the fundus of the examined eye 12 is not completely expressed by information acquired by the OCT system but is incomplete.

Figure 4:
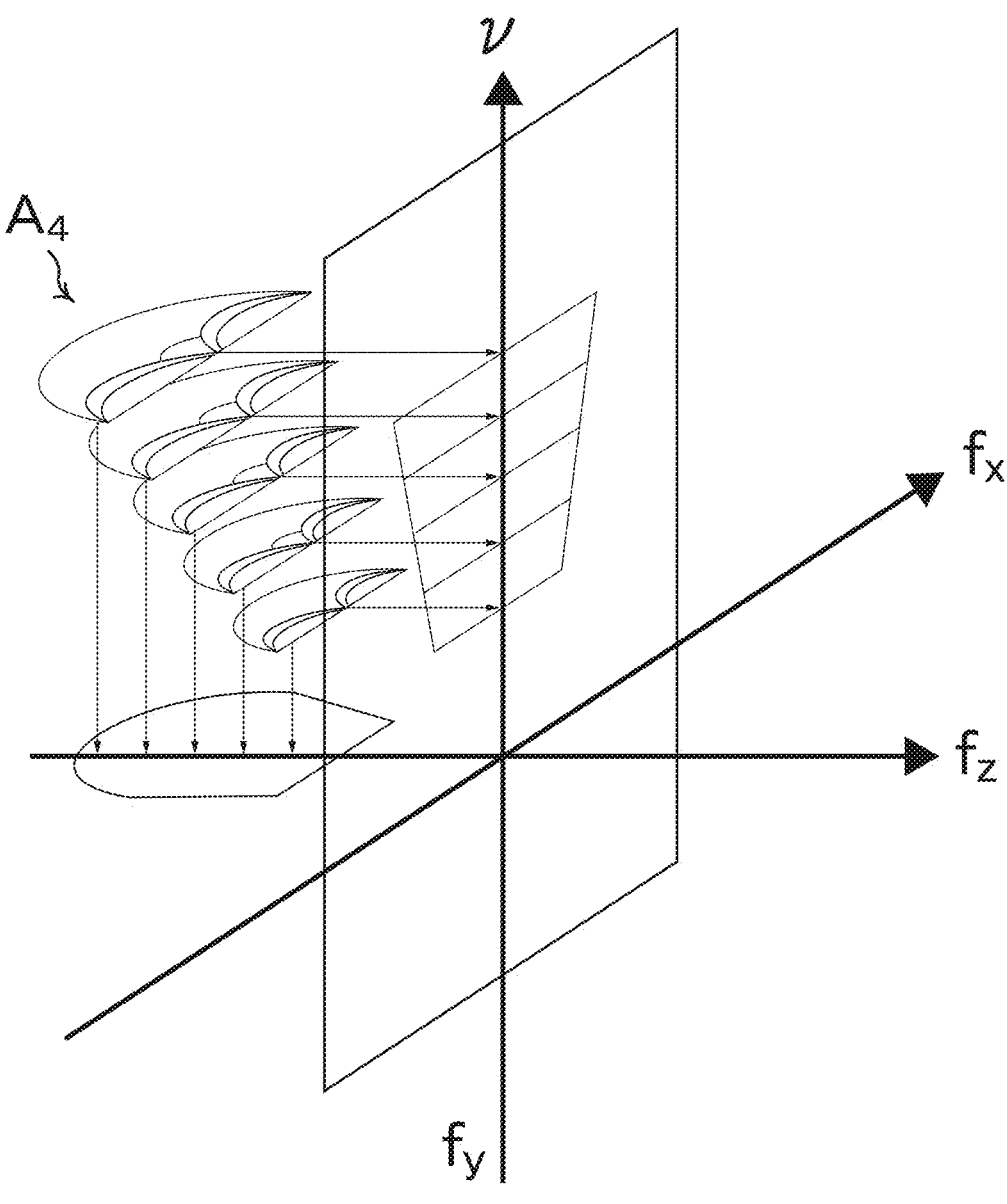
FIG. 4 is a conceptual view of an example depicting information relating to an OCT image in a four-dimensional frequency space of an OCT system.

FIG. 4 shows an example of information relating to an OCT image. FIG. 4 is an example in which information relating to an OCT image focused by an optical system of an OCT system, based on an optical system (for example, an objective lens) with NA=0.9 is depicted in a four-dimensional frequency space. In FIG. 4, υ represents frequencies of light from the light source 20A (in the present exemplary embodiment, frequencies of light illuminated onto the fundus), and fx, fy and fz represent object frequencies (in the present exemplary embodiment, frequencies of light reflected from the fundus). Angular velocities ω may be employed as the frequencies υ (ω=2πυ). To simplify description, the object frequency fy axis is not shown. FIG. 4 depicts an example in which optical paths of the optical system (for example, objective lenses) of the OCT system are the same. That is, an optical path for illumination of the measurement light and an optical path for reflected light from the examined eye 12 are the same, and NA=0.9 for both.

The object frequencies (fx, fy and fz) are consistent in the u direction. Frequencies in real space are in a predetermined range specified in advance in the four-dimensional frequency space. Accordingly, a window function representing a 4-D aperture $A_4$ (a four-dimensional aperture) is defined as an instrumental function of the OCT system. The 4-D aperture $A_4$ is an aperture space in the four-dimensional frequency space. Of object frequencies, the OCT system acquires only frequencies in the 4-D aperture $A_4$. However, not all frequencies are acquired in the 4-D aperture $A_4$ (four-dimensional information); three-dimensional information is acquired with frequencies in the fz direction being integrated at the time of detection. When the frequencies in the 4-D aperture $A_4$ are integrated in the fz direction, some of the four-dimensional information is lost.

Accordingly, the present exemplary embodiment provides an OCT system that is capable of reducing information loss that loses some of the four-dimensional information.

In, for example, a system such as an interference microscope or the like that is capable of three-dimensional scanning, frequencies of an object are integrated over υ in the 4-D aperture $A_4$. Therefore, the information loss by which some of the four-dimensional information is lost may be reduced by employing integrals over υ of object frequencies in the 4-D aperture $A_4$.

In the present exemplary embodiment, as an OCT system that reduces information loss, an optical system is provided that makes the 4-D aperture $A_4$ significantly narrower. Hence, even with integration over fz, the information loss losing some of the four-dimensional information may be reduced. More specifically, an optical system is formed such that the NA of an illumination side optical system for illuminating light onto the examined eye 12 and the NA of a detection side optical system for detecting light from the examined eye 12 (for example, light reflected from the fundus) are different numerical apertures. For example, the 4-D aperture $A_4$ may be formed to be narrower such that the NA of the illumination side optical system for light toward the examined eye 12 is made thoroughly small, for example, substantially zero, and the NA of the detection side optical system for light from the examined eye 12 is greater than the NA of the illumination side optical system. In the present exemplary embodiment, the NA of an optical system that is thoroughly small is referred to as "an NA of zero (NA=0)". That is, optical systems with an NA of zero encompass an optical system with an NA greater than zero but with an aperture angle smaller than the height of an image formed by light flux. Optical systems with an NA of zero also encompass, for example, an optical system formed such that incident light or emitted light has parallel light flux and the NA can be regarded as zero.

An optical system with an NA of zero may be employed as an optical system of an OCT system based on full field illumination that uniformly illuminates an object at an illuminated side, such as the examined eye 12 or the like, or block illuminates a predetermined region of an object at the illuminated side.

When the 4-D aperture $A_4$ is formed to be narrow, object frequencies in the 4-D aperture $A_4$ have sufficient information amounts (including fz information), and the information loss that loses some of the information (four-dimensional information) relating to the examined eye 12 may be reduced even when integrated over fz.

Figure 5:
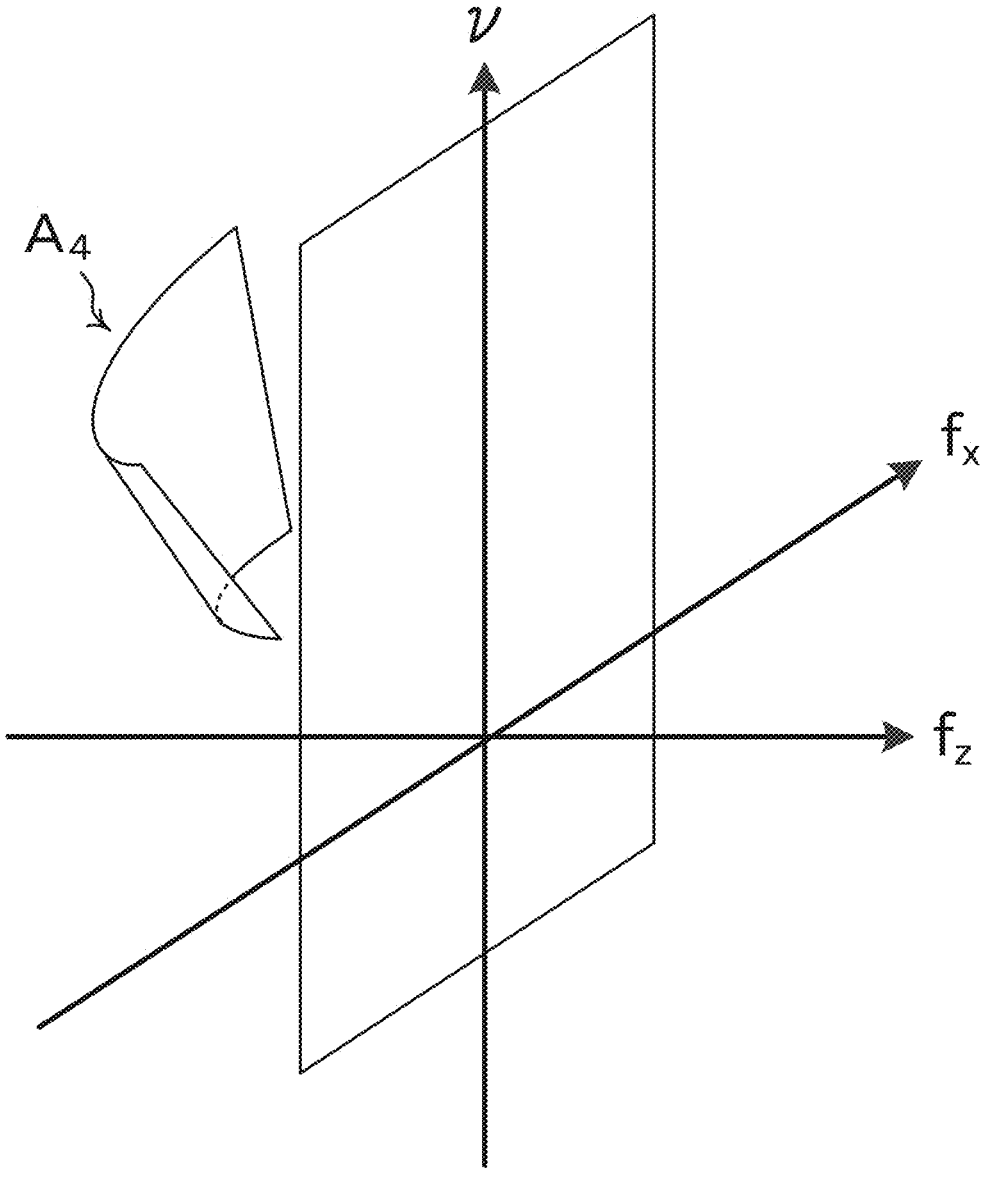
FIG. 5 is a conceptual diagram depicting an example of a 4-D aperture $A_4$.
Figure 6:
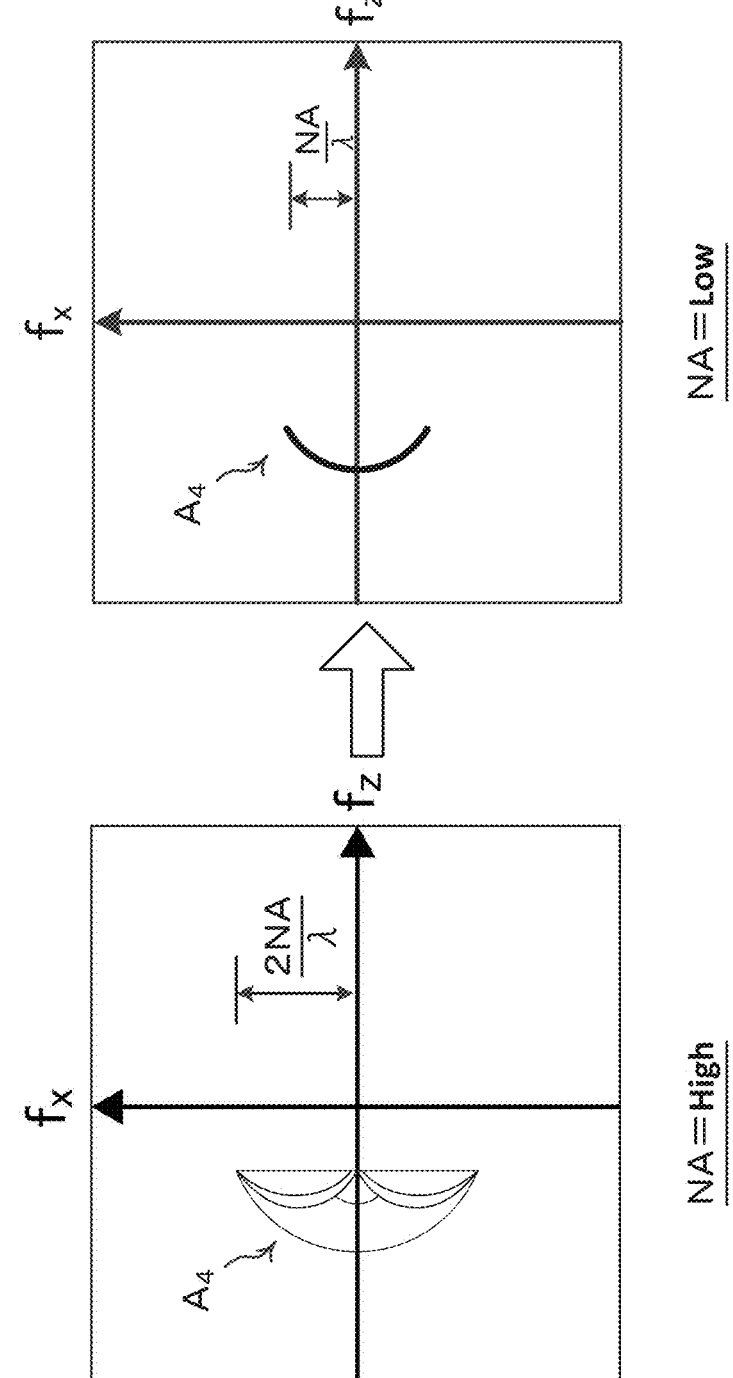
FIG. 6 is a conceptual diagram depicting a portion of the 4-D aperture $A_4$.

That is, in the present exemplary embodiment the optical system is formed such that the NA of the illumination side optical system and the NA of the detection side optical system are different. More specifically, the optical system is formed such that the NA of the illumination side optical system is thoroughly small, forming an optical system with an NA of zero, and the NA of the detection side optical system is larger than the NA of the illumination side optical system. Thus, as illustrated in FIG. 5, the 4-D aperture $A_4$ may be formed to be narrow. More specifically, as illustrated by the 4-D aperture $A_4$ for a certain frequency (a frequency $\upsilon$ of light from the light source 20A) in FIG. 6, a shape including information in the fz direction (the semicircular shape in FIG. 6) is a linear shape. Apertures with this linear shape are connected to form the 4-D aperture $A_4$ of the present exemplary embodiment (FIG. 5).

An optical system for forming the 4-D aperture $A_4$ to be narrow includes one optical system with an NA of zero or close to zero and another optical system with an NA larger than the NA of the one optical system. For example, as an example of a thoroughly small NA of an optical system of a microscope or the like, NA=0.2. Accordingly, as the condition of the NA being small in the present exemplary embodiment with a view to forming the 4-D aperture $A_4$ to be narrow, it is preferable if the NA of the illumination side optical system, the excitation side, satisfies the following relationship.

$$0 \leq NA \leq 0.2$$

The 4-D aperture $A_4$ that is formed to be narrow is an example of a four-dimensional frequency aperture of the technology of the present disclosure.

As an example below, a configuration is described in which the illumination side optical system for light toward the examined eye 12 is an optical system with an NA of zero and the detection side optical system for light from the examined eye 12 is an optical system with an NA of a finite value, but the technology of the present disclosure is not limited thus. For example, the detection side optical system may be an optical system with an NA of zero and the illumination side optical system may be an optical system with an NA of a finite value. An above-mentioned optical system with an NA of zero may have an NA with a finite value. That is, as long as an optical system is formed such that the NA of the illumination side optical system is different from the NA of the detection side optical system, because the two NAs are different, the 4-D aperture $A_4$ may be formed to be narrower than if the two NAs were the same.

Figure 7:
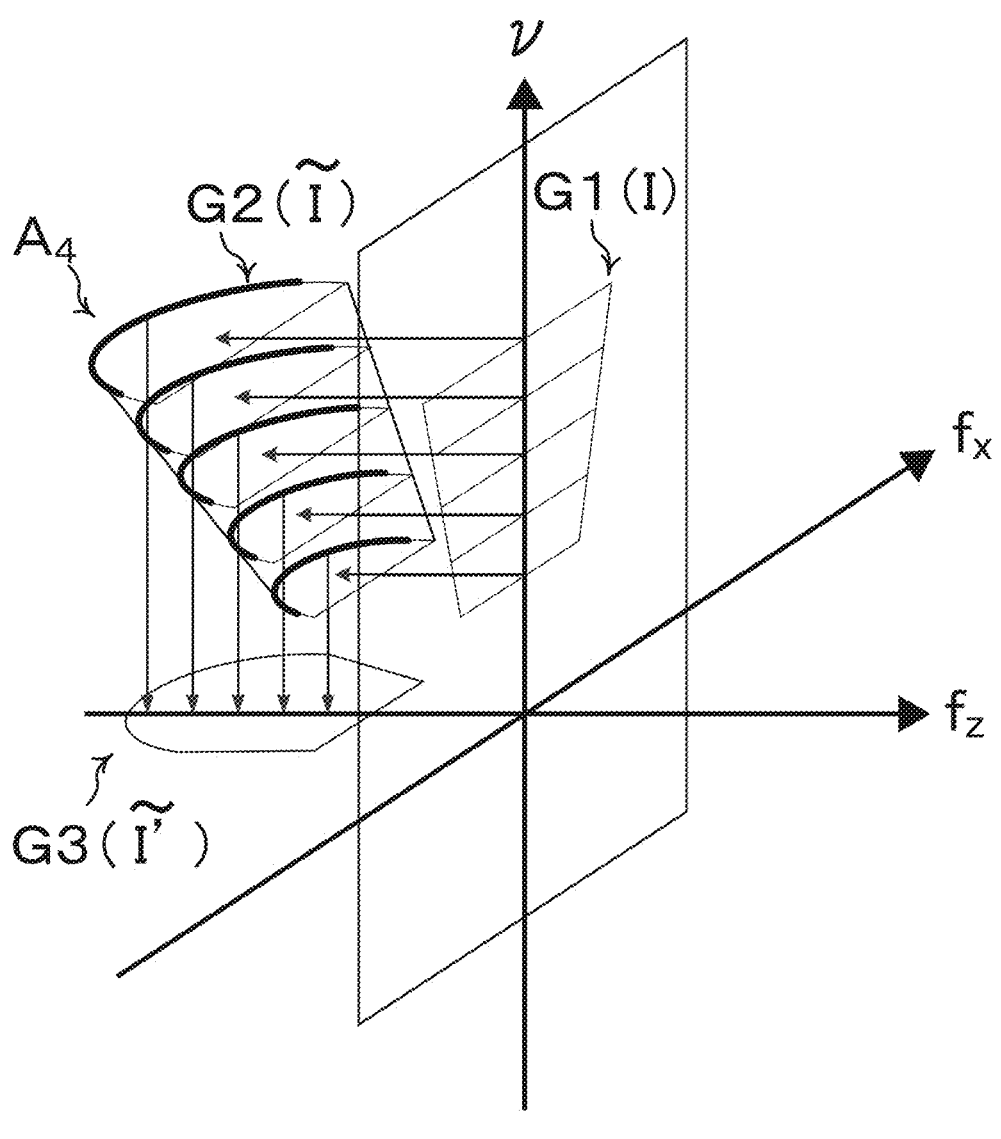
FIG. 7 is an explanatory diagram depicting a concept of correction processing of an OCT image by a double projection method.

In the present exemplary embodiment, the 4-D aperture $A_4$ that is capable of reducing information loss is utilized and an OCT image is corrected. That is, frequency information in the OCT image is utilized and the OCT image is corrected by a method that performs processing in two stages (a double projection method). As is conceptually illustrated in FIG. 7, in the processing of a first stage of the processing to correct an OCT image, processing is performed to project frequency information (I) of an OCT image G1 onto the narrowly formed 4-D aperture $A_4$. In the processing of the second stage, processing is performed to project information (~I) of the image G2 that has been projected onto the 4-D aperture $A_4$ in the $\upsilon(=2\pi/\omega)$ direction, that is, onto (fx, fy, fz) planes. Information (~I') of the image G3 that has been projected by the second stage of processing has a reduced information loss from the information (four-dimensional information) relating to the examined eye 12. Therefore, for example, a distorted OCT image may be corrected to an image equivalent to a usual microscope image by the double projection method described above. Because the information loss is reduced, resolution is maintained and OCT images may be generated at higher resolution than in a configuration that does not utilize the narrowly formed 4-D aperture $A_4$.

That is, the 4-D aperture $A_4$ (four-dimensional aperture) is defined by the optical system with the first numerical aperture and the optical system with the second numerical aperture, which are quantities that are independent of object frequencies. In the present exemplary embodiment, the four-dimensional aperture may be realized as a window function that may represent physical quantities set by the structure of the optical system of the OCT system. In the present exemplary embodiment, object frequencies are physical quantities that represent the examined eye 12 by light components. Because the object frequencies are not dependent on $\upsilon$, the object frequencies are consistent four-dimensional physical quantities in the $\upsilon$ direction. The frequencies $\upsilon$ are light frequencies of the light source and also light frequencies of signal light. The object frequencies are multiplied with the 4-D aperture $A_4$ to provide a four-dimensional function (image frequencies that can be acquired). A three-dimensional function is obtained by integration over fz of the four-dimensional function. Values of the three-dimensional function are acquired as detection values by the optical system. In other words, values of the three-dimensional function representing integration over fz of the four-dimensional function, in which the 4-D aperture $A_4$ is multiplied with the object frequencies, are acquired by a sensor of the optical system of the OCT system.

When an NA value is a finite value, the 4-D aperture $A_4$ has a finite thickness. Accordingly, when the 4-D aperture $A_4$ with the finite thickness is utilized, it is appropriate to set and utilize an aperture plane within the 4-D aperture $A_4$. As this aperture plane, it is preferable to employ a predetermined plane separated from an origin point in the 4-D aperture $A_4$ (for example, an outermost plane of the 4-D aperture $A_4$, which is a plane that is furthest from the origin point in the 4-D aperture $A_4$).

Information of frequencies of an OCT image utilizing the 4-D aperture $A_4$ described above, to be used in correction of the OCT image, may be represented by the following expression (1).

$$I(x, y, z, \tau)|_{z'=0} = \int\int\int\int \tilde{\eta}(f_x, f_y, f_z)A_4(f_x, f_y, f_z, v) \qquad (1)$$
$$e^{-i2\pi(f_x x + f_y y + f_z z - v\tau)} df_x df_y df_z dv\big|_{z=0}$$
$$= \int\int\int\int \tilde{\eta}(f_x, f_y, f_z)A_4(f_x, f_y, f_z, v)$$
$$df_z e^{-i2\pi(f_x x + f_y y - v\tau)} df_x df_y dv$$

In this expression, t represents distances in the depth direction of the examined eye 12 (in time-domain OCT as an example, an adjustment amount by which an optical path length of the reference light optical system 20D is adjusted, for example, a movement amount of a mirror).

Information (~I) of the image G2 projected onto the 4-D aperture $A_4$ may be represented by the following expression (2).

$$\tilde{I}(f_x, f_y, v) = \int \tilde{\eta}(f_x, f_y, f_z)A_4(f_x, f_y, f_z, v)df_z \qquad (2)$$

Information (~I') of the image G3 projected from the 4-D aperture $A_4$ may be represented by the following expression (3).

$$\tilde{I}'(f_x, f_y, f_z) = \int \tilde{I}(f_x, f_y, v)A_4(f_x, f_y, f_z, v)dv \qquad (3)$$

The control device 16 uses the image processing device 17 operating under the control of the CPU 16A and utilizes the above expressions (1) to (3) to generate OCT images. Processing that generates the OCT images is described below.

Now, structures of the optical system of the OCT system relating to the present exemplary embodiment are described with reference to FIG. 8. In order to simplify description, the wide-angle optical system 30 is not shown in FIG. 8.

The sensor 20B of the OCT unit 20 is equipped with a pair of lenses 20B-1 and a detection component 20B-2. The sensor 20B collimates light split by the first light coupler 20C, which is to say interference light in which measurement light reflected by a fundus interferes with the reference light, to parallel light with the pair of lenses 20B-1 and then causes the light to converge on the detection component 20B-2.

The reference light optical system 20D is equipped with a pair of lenses 20D-1 and a mirror 20D-2. The reference light optical system 20D collimates light split by the first light coupler 20C, which is to say the reference light, to parallel light with the pair of lenses 20D-1 and then causes the light to converge on the mirror 20D-2. The mirror 20D-2 is structured to be movable in the optical axis direction (the direction indicated by arrow t in FIG. 8). Reflected light that is reflected by the mirror 20D-2 is returned to the first light coupler 20C via the pair of lenses 20D-1 to serve as the reference light.

Figure 8:
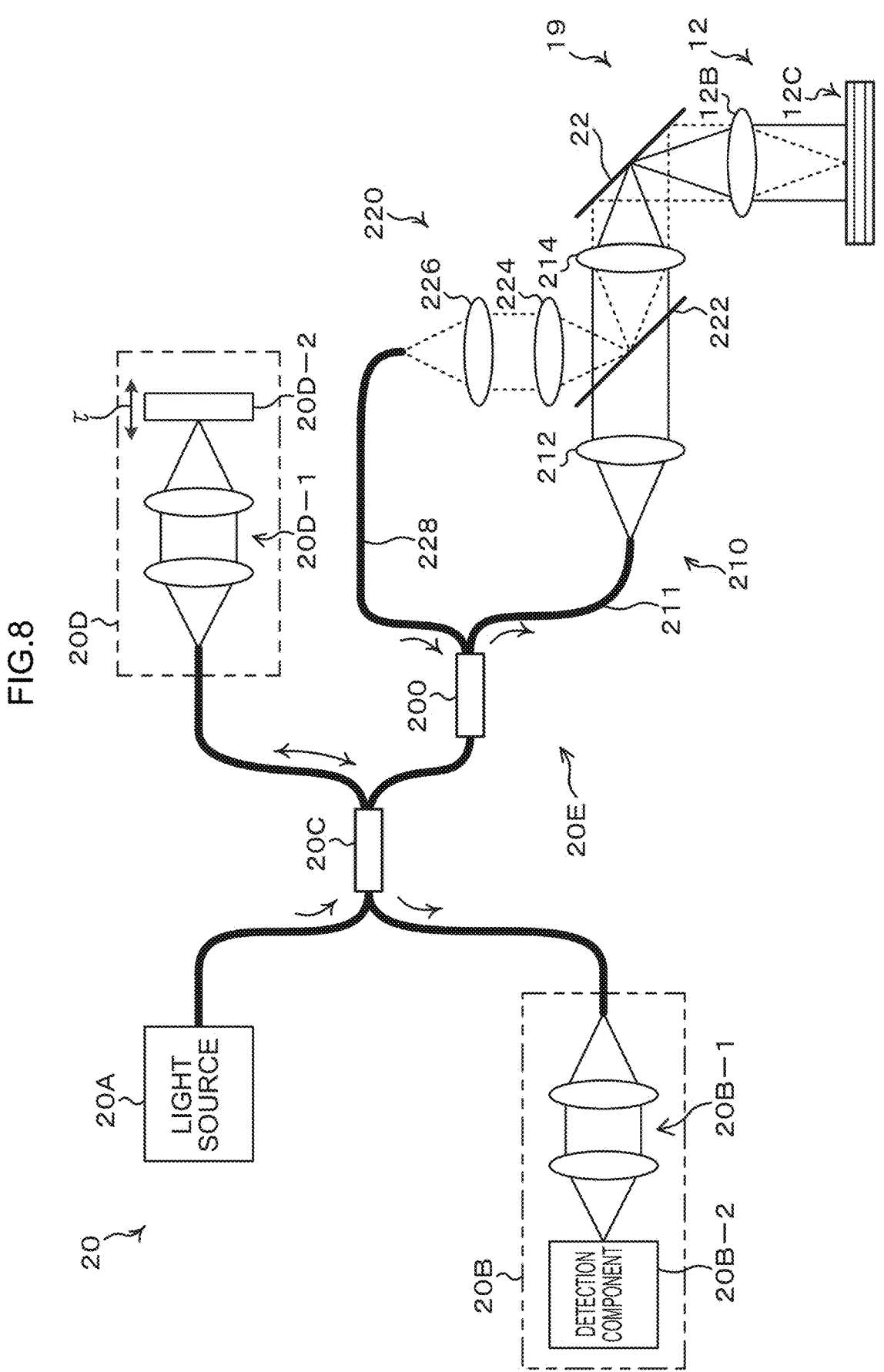
FIG. 8 is a conceptual structural diagram of an optical system of the OCT system.

A structure in which the mirror 20D-2 serving as the reference light optical system 20D is movable is employed in FIG. 8, but the OCT system according to the present exemplary embodiment is not limited to a structure in which the mirror 20D-2 is movable; the mirror 20D-2 may be fixed. That is, the OCT system according to the present exemplary embodiment is applicable to various types of OCT system, such as time domain OCT (TD-OCT), swept-source OCT (SS-OCT) and spectral domain OCT (SD-OCT) employing a spectroscope, which are wavelength-sweeping types known as Fourier domain OCT, and so forth.

Therefore, it is sufficient that the OCT system be structured in accordance with the type of OCT system to be employed. For example, when time-domain OCT (TD-OCT) is to be employed, a structure that moves to sweep the mirror 20D-2 is appropriate. When an SD-OCT type of Fourier domain OCT is to be employed, fixing the mirror 20D-2 and employing spectroscopic detection is appropriate. For spectroscopic detection, it is appropriate to use a light source that emits plural lights with plural wavelengths. When SS-OCT is employed, for example, using a one-pixel detector at the detection component 20B-2, fixing the mirror 20D-2, and sweeping the wavelength of a wide-band light source is appropriate. For sweeping through wavelengths, it is appropriate to use, for example, a wide-band light source based on a laser device that emits wide-band laser light for wavelength sweeping as the light source 20A. As an optical system with an NA of zero, an optical system of an OCT system based on full field illumination that uniformly illuminates a body at the illuminated side, such as the examined eye 12 or the like, or block illuminates a predetermined region of the object at the illuminated side may be employed. That is, the technology of the present disclosure is not limited to the above-described laser scanning-type optical system that scans laser light. An optical system that uses a charge-coupled device (CCD) camera or the like may be employed for the optical system. In this case, using a CCD camera that includes a component such as a CCD or the like at the detection component 20B-2 is appropriate.

The emission and detection optical system 20E includes the second light coupler 200, an illumination optical system 210 and a detection optical system 220. The second light coupler 200 has a function of guiding light emitted from the light source 20A (measurement light that has been split by the first light coupler 20C) into the illumination optical system 210 to serve as light for measurement, and a function of guiding light from the detection optical system 220 (that is, light returning from the examined eye 12) into the first light coupler 20C (that is, toward the sensor 20B) to serve as light for detection. Therefore, light transmitted through the illumination optical system 210 that is light from the light source 20A is illuminated onto the examined eye 12, and returning light of the light that has been transmitted through the illumination optical system 210 and illuminated onto the examined eye 12 (light reflected by the examined eye 12) is transmitted through the detection optical system 220 and is incident on the sensor 20B as the measurement light. In the emission and detection optical system 20E in FIG. 8, light paths according to the illumination optical system 210 are depicted as solid lines and light paths according to the detection optical system 220 are depicted as dotted lines.

The illumination optical system 210 is equipped with a pair of lenses: a lens 212 and a lens 214. The lens 212 is disposed on the optical axis of the illumination optical system 210 such that one end face of an illumination side fiber 211 is disposed at an incidence side focusing position of the lens 212. The illumination side fiber 211 is formed by a single-mode fiber. The other end face of the illumination side fiber 211 is connected to the second light coupler 200.

The lens 214 is disposed on the optical axis of the illumination optical system 210 such that a reflection surface of the optical scanner 22 is disposed at an emission side focusing position of the lens 214. Therefore, the lens 212 collimates light from the light source 20A (the measurement light split by the first light coupler 20C) to parallel light, and the lens 214 converges the parallel light collimated by the lens 212 onto the reflection surface of the optical scanner 22. Light reflected by the optical scanner 22 is then collimated to parallel light by a lens 12B of the examined eye 12 and illuminated onto a fundus 12C. Thus, light from the light source 20A via the illumination optical system 210 is illuminated onto the fundus 12C of the examined eye 12 as parallel light.

The illumination optical system 210, being an optical system that emits parallel light toward the examined eye 12, forms an optical system with an NA of zero. The NA of the illumination optical system 210 is an example of a "first numerical aperture" of the technology of the present disclosure. The illumination optical system 210 is an example of an "optical system with the first numerical aperture" of the technology of the present disclosure.

The detection optical system 220 includes a beam splitter 222 and a pair of lenses: the lens 224 and a lens 226. The beam splitter 222 is disposed between the lens 212 and lens 214 of the illumination optical system 210. The beam splitter 222 extracts light returning from the examined eye 12 (reflected light) by means of a reflection function. The beam splitter 222 is disposed such that a reflection surface of the beam splitter 222 is disposed on the optical axis of the illumination optical system 210 at an emission side focusing position of the lens 214 for light returning from the examined eye 12 (the reflected light). A lens 224 is disposed on the optical axis of the detection optical system 220 such that the reflective surface of the beam splitter 222 is disposed at an incidence side focusing position of the lens 224. A lens 226 is disposed on the optical axis of the detection optical system 220 such that one end face of a detection side fiber 228 is disposed at an emission side focusing position of the lens 226. The detection side fiber 228 is formed by a single-mode fiber. The other end face of the detection side fiber 228 is connected to the second light coupler 200. The lens 224 collimates light from the beam splitter 222 to parallel light, and the lens 226 converges the parallel light collimated by the lens 224 onto the end face of the detection side fiber 228. Thus, light reflected at points of the fundus 12C of the examined eye 12 is emitted from the detection optical system 220 toward the sensor 20B.

The detection optical system 220, being an optical system with a focusing point at the side thereof at which the examined eye 12 is disposed, forms an optical system with an NA different from the illumination optical system 210, which is an NA with a finite value. The NA of the detection optical system 220 is an example of a "second numerical aperture" of the technology of the present disclosure. The detection optical system 220 is an example of an "optical system with the second numerical aperture" of the technology of the present disclosure.

The ophthalmological device 110 of the present exemplary embodiment uses the OCT system including the illumination optical system 210 with an NA of zero described above to generate an OCT image based on information in which information loss of the obtained four-dimensional information is reduced. Operating under the control of the CPU 16A, the image processing device 17 is used to generate OCT images by execution of the image processing program. In the present exemplary embodiment, generation of OCT images in the ophthalmological device 110 is described, but clearly an OCT image may be generated by an external device such as the server 140 or the like.

Figure 10:
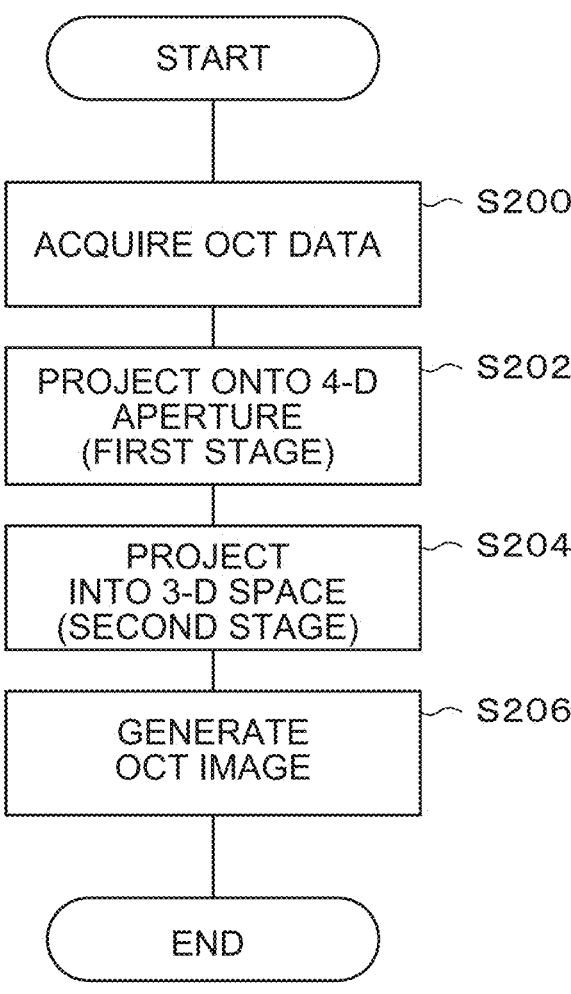
FIG. 10 is a flowchart showing an example of a flow of image processing.

The image processing program illustrated in FIG. 10 is memorized at the ROM 16C of the ophthalmological device 110 or the memory 17M of the image processing device 17.

The ROM 16C and the memory 17M are examples of "memory" of the technology of the present disclosure. The CPU 16A is an example of a "processor" of the technology of the present disclosure. The image processing program is an example of a "program" of the technology of the present disclosure.

Figure 9:
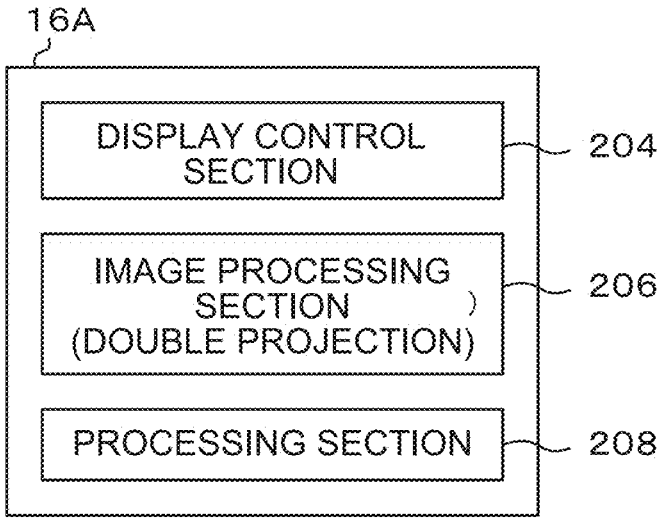
FIG. 9 is an explanatory diagram of functions realized by an image processing program.

In the ophthalmological device 110 according to the present exemplary embodiment, the CPU 16A realizes various functions by reading and executing the image processing program. The image processing program includes a display control function, an image processing function and a processing function. That is, by executing the image processing program with these functions, the CPU 16A operates as a display control section 204, an image processing section 206 and a processing section 208, as shown in FIG. 9. The image processing function includes an image processing function based on a method that performs the two-stage processing described above (the double projection method).

Now, details of the image processing according to the present exemplary embodiment are described using FIG. 10. The CPU 16A of the ophthalmological device 110 executes the image processing depicted in the flowchart of FIG. 10 by reading the image processing program from the ROM 16C or memory 17M and executing the image processing program.

The processes of the image processing illustrated in FIG. 10 are an example of an image processing method of the present disclosure.

In step S200, the image processing section 206 of the CPU 16A acquires OCT data from the image processing device 17. The OCT data is data obtained by OCT imaging of the examined eye 12 by the ophthalmological device 110. The OCT data includes data for positions with different depths in the optical axis direction (the Z axis direction). The OCT data is obtained by OCT imaging by the ophthalmological device 110 as described above.

In step S202, the image processing section 206 executes the first stage of processing, projecting the information (OCT data) obtained by the OCT system onto a four-dimensional aperture. That is, the image processing section 206 uses the above-mentioned expression (1) to represent the acquired OCT data and, as processing to project information (I) of frequencies of an OCT image G1 onto the narrowly formed 4-D aperture $A_4$, the image processing section 206 uses the above-mentioned expression (2) to derive frequency information of the OCT image. The derived information is temporarily stored in the RAM 16B.

Then, in step S204, the image processing section 206 executes the second stage of processing, projecting the information projected onto the 4-D aperture $A_4$ into three-dimensional space. That is, the image processing section 206 performs processing to project information ($\sim$I) of the image G2 that has been projected onto the 4-D aperture $A_4$ in the $\upsilon$ ($=2\pi/\omega$) direction (in the (fx, fy, fz)) planes). In the second stage of processing, as the processing to project the OCT data projected onto the 4-D aperture $A_4$ into three-dimensional space, the image processing section 206 uses the above-mentioned expression (3) to derive information of the double-projected OCT image that has been projected from the 4-D aperture $A_4$ into three-dimensional space. The derived information is temporarily stored in the RAM 16B.

Then, in step S206, the image processing section 206 uses the information projected by the double projection method to generate an OCT image. The generated OCT image is stored in the RAM 16B by the processing section 208.

The OCT image that has been corrected using the double projection method described above may generate an OCT image for a depth that is a position specified in advance in the optical axis direction, that is, the depth direction of the examined eye 12, and may generate OCT images for depths that are plural different positions. For example, by reference to the focusing position of the detection optical system 220 at the side thereof at which the examined eye 12 is disposed, an OCT image may be generated for a position at a depth predetermined so as to be at ten times the depth of focusing from the focusing position, or the like. Plural OCT images may be generated for each of different depths by reference to the focusing position, and OCT images may be generated for a plural number of positions with a predetermined spacing. When plural OCT images are generated, storing each of the plural OCT images in the RAM 16B or memory 17M is appropriate. The predetermined depths, different depths and predetermined numbers may be set in advance and may, for example, be arbitrarily specified by a user.

When the OCT images described above are generated, in order to improve clarity of the images, image processing for noise removal and the like may be carried out.

As described above, by the image processing section 206 executing the image processing illustrated in the flowchart of FIG. 10, for example, OCT images are generated for positions at predetermined depths by reference to the focusing position of the detection optical system 220 at the side at which the examined eye 12 is disposed. The generated OCT images have reduced information loss and maintain resolution. Thus, the generated OCT images are high-resolution OCT images that faithfully portray conditions of the fundus of the examined eye 12.

In the image processing described above, processing to generate information for a display screen that displays the generated OCT images may be added. Processing to generate information for a display screen displaying the OCT images may generate information for the display screen to display an array of OCT images that are samples determined in advance. When plural OCT images are generated, information for the display screen to display the array of the plural OCT images may be generated. When control is performed to display an array of plural OCT images, for example, information for the display screen to display an OCT image group arrayed in a direction of increasing depth may be generated. Thus, changes in size, shape and the like of the examined eye 12 in the depth direction may be visualized and presented to a user.

Figure 11A:
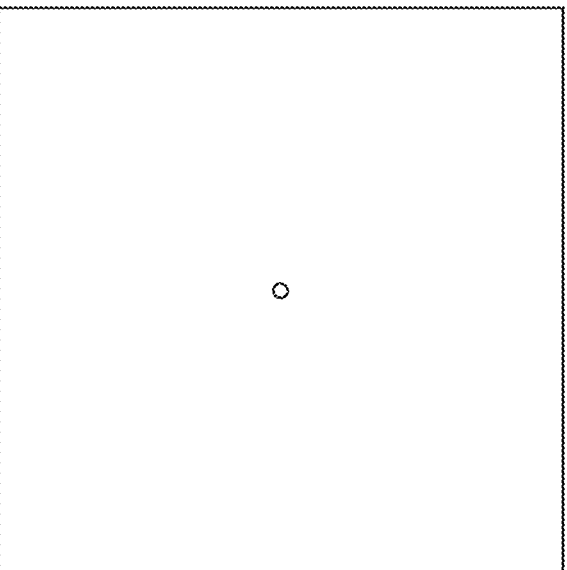
FIG. 11A is a conceptual diagram showing an example of an OCT image according to the present exemplary embodiment.
Figure 11B:
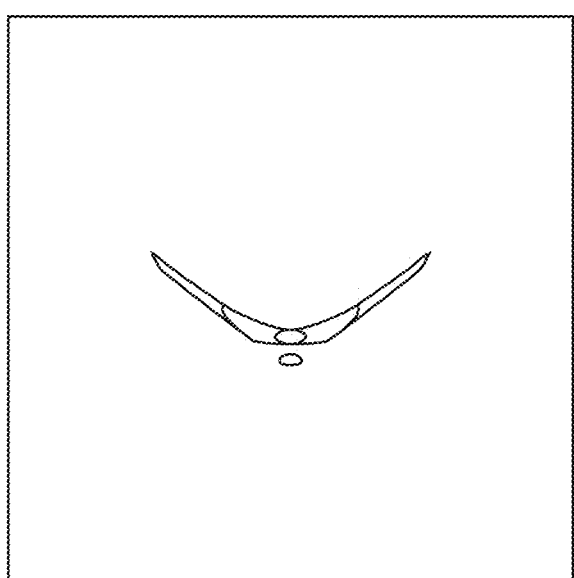
FIG. 11B is a conceptual diagram showing a comparative example of the OCT image.

From information of a point detected by the ophthalmological device 110, an OCT image obtained by correction using the double projection method described above is corrected from, for example, an OCT image that is distorted as illustrated in FIG. 11B to an OCT image equivalent to a usual microscope image as illustrated in FIG. 11A. FIG. 11A is an OCT image when the emission and detection optical system 20E of the OCT unit 20 is formed such that the NA of the illumination optical system 210 and the NA of the detection optical system are different and the OCT image is corrected by the double projection method. Here, the NA of the illumination optical system 210 illuminates parallel light flux onto the examined eye, forming an optical system with an NA of zero, and the detection optical system 220 forms an optical system such that the NA is 0.9. FIG. 11A is an OCT image generated at a depth position that is separated by a distance of 30 times the depth of focus. As a comparative example in FIG. 11B, the illumination optical system 210 and the detection optical system 220 are formed such that the NA of the illumination optical system 210 and the NA of the detection optical system 220 match at 0.9.

As shown in FIG. 11A, because the OCT system according to the present exemplary embodiment is employed, an OCT image may be obtained as an image of one point (a point image) from information of one point of the examined eye 12 that is detected. As shown in FIG. 11B, when the NAs of the illumination optical system 210 and the detection optical system 220 match, the OCT image has a distorted shape, and an image in which the shape of the fundus of the examined eye 12 is deformed is obtained. Accordingly, as can be seen from FIG. 11A and FIG. 11B, a high-precision OCT image may be generated by forming the 4-D aperture $A_4$ to be narrow and generating an OCT image from information by the double projection method that projects the information via the 4-D aperture $A_4$.

As described above, according to the present exemplary embodiment, the illumination optical system 210 and the detection optical system 220 have different NAs, and the NA of one of the optical systems (the illumination optical system 210 in the descriptions above) is zero. Therefore, an aperture relating to an OCT image in a four-dimensional space that considers frequencies may be treated as a narrow aperture (the 4-D aperture $A_4$) that is capable of suppressing the effect of integration over fz. In information of an OCT image projected by the double projection method using this narrowly formed 4-D aperture $A_4$, an information loss of information (four-dimensional information) relating to the examined eye 12 is reduced. Therefore, the OCT image may be corrected by the image processing described above and, for example, a distorted OCT image may be corrected to an image equivalent to a usual microscope image. Because the information loss is reduced, resolution is maintained and OCT images may be generated at higher resolution than in a configuration that does not utilize the narrowly formed 4-D aperture $A_4$.

In the exemplary embodiment described above, the image processing (FIG. 10) is described as being executed by the ophthalmological device 110, but the technology of the present disclosure is not limited thus. The image processing may be executed by any of the ophthalmological device 110, the server 140, the viewer 150, an additional image processing device that is also provided on the network 130, or by a combination of these.

In the technology of the present disclosure as described above, it is preferable if the image processing is executed using information obtained utilizing the narrowly formed 4-D aperture $A_4$. Therefore, the technology of the present disclosure encompasses the technologies described below.

—First Technology—

An image processing device including: an acquisition section that acquires information representing interference light that is obtained by illuminating light from a light source through an optical system with a first numerical aperture onto an illuminated side object, transmitting signal light returning from the illuminated side object in response to the illuminated light through an optical system with a second numerical aperture, dividing a reference light from the light from the light source, and detecting the interference light between the signal light and the reference light; and a processing section that performs a first process of projecting the information representing the interference light onto a four-dimensional frequency aperture formed by the optical system with the first numerical aperture and the optical system with the second numerical aperture in a four-dimensional space of frequencies of the light source and frequencies of light in three dimensions representing the illuminated side object, and a second process of projecting the information projected by the first process into three-dimensional space.

The image processing section 206 is an example of the acquisition section and the processing section of the technology of the present disclosure.
—Second Technology—

An ophthalmological device including: a detection unit that detects interference light between signal light that is obtained by illuminating light from a light source at an examined eye and reference light that is divided from the light from the light source; an illumination optical system formed with a first numerical aperture so as to illuminate the light from the light source onto the examined eye; a detection optical system formed with a second numerical aperture so as to transmit light returning from the examined eye in response to the light illuminated through the illumination optical system, the detection optical system transmitting the returning light to the detection section as the signal light, and the second numerical aperture being different from the first numerical aperture; a processing section that performs processing on the basis of information representing the interference light detected by the detection section, the processing including a first process of projecting the information representing the interference light onto a four-dimensional frequency aperture formed by the optical system with the first numerical aperture and the optical system with the second numerical aperture in a four-dimensional space of frequencies of the light source and frequencies of light in three dimensions representing the examined eye, and a second process of projecting the information projected by the first process into three-dimensional space; and an image generation section that, on the basis of the information processed by the processing section, generates a plurality of images corresponding to a plurality of planes at different depths in an optical axis direction.

The sensor 20B is an example of the acquisition section of the technology of the present disclosure. The illumination optical system 210 is an example of the illumination optical system of the technology of the present disclosure, and the detection optical system 220 is an example of the detection optical system of the technology of the present disclosure. The image processing section 206 is an example of the processing section and the image processing section of the present technology of the present disclosure.

Hereabove, the present disclosure has been described using an exemplary embodiment, but the technical scope of the present disclosure is not to be limited to the scope described in the above exemplary embodiment. Numerous modifications and improvements may be applied to the exemplary embodiment described above within a scope not departing from the gist of the invention, and modes in which these modifications and/or improvements are applied are to be encompassed by the technical scope of the disclosure.

In the exemplary embodiment described above, processing is described as being implemented by the execution of a program memorized at a memory device such as a memory or the like, but at least a portion of the processing of a program may be implemented in hardware. Further, the flow of the processing of the program described in the above exemplary embodiment is an example. Unnecessary steps may be removed, new steps may be added, and the processing sequence may be rearranged within a scope not departing from the gist of the disclosure.

To cause execution of the processing according to the exemplary embodiment described above by a computer, a program describing code that enables a computer to carry out the processing described above may be memorized and distributed on a recording medium such as an optical disc or the like.

The above exemplary embodiment is described as using a CPU as an example of a general purpose processor, but the term "processor" refers to processors in a broad sense, encompassing general purpose processors (for example, a central processing unit (CPU) or the like), dedicated processors (for example, a graphics processing unit (GPU), application-specific integrated circuit (ASIC), field programmable gate array (FPGA), programmable logic device or the like) and so forth.

Operations of the processor of the exemplary embodiment described above need not be conducted by a single processor but may be conducted by plural processors in co-operation, and may be conducted in co-ordination by plural processors at physically distant locations.

All references, patent applications and technical specifications cited in the present specification are incorporated by reference into the present specification to the same extent as if the individual references, patent applications and technical specifications were specifically and individually recited as being incorporated by reference. The disclosures of Japanese Patent Application No. 2022-048770 filed Mar. 24, 2022 are incorporated into the present specification by reference in their entirety.

The invention claimed is:

1. An image processing method to be carried out by a processor at an image processing device, the image processing method comprising:

acquiring information representing interference light that is obtained by
  illuminating light from a light source through an optical system with a first numerical aperture onto an illuminated side object,
  transmitting signal light returning from the illuminated side object in response to the illuminated light through an optical system with a second numerical aperture,
  dividing a reference light from the light from the light source, and
  detecting the interference light between the signal light and the reference light; and
performing processing including:
  a first process of projecting the information representing the interference light onto a four-dimensional frequency aperture formed by the optical system with the first numerical aperture and the optical system with the second numerical aperture in a four-dimensional space of frequencies of the light source and frequencies of light in three dimensions representing the illuminated side object, and
  a second process of projecting the information projected by the first process into three-dimensional space.

2. The image processing method according to claim 1, wherein:

the image processing device is provided at an ophthalmological device, and
the illuminated side object is an eye to be examined.

3. The image processing method according to claim 1, wherein:

the information representing the interference light is OCT data obtained by detection at a detection unit that is included in the image processing device and that detects interference light for optical coherence tomography, and the information representing the interference light that the processor acquires is the OCT data.

4. The image processing method according to claim 3, wherein the information representing the interference light employs the OCT data obtained by detection at the detection unit that detects interference light for time-domain optical coherence tomography or Fourier-domain optical coherence tomography.

5. The image processing method according to claim 3, wherein the processor generates a plurality of images corresponding to a plurality of planes at different depths, based on the OCT data.

6. The image processing method according to claim 1, wherein the processor acquires the information representing the interference light by obtaining the signal light from the optical system with the first numerical aperture and the optical system with the second numerical aperture, the first numerical aperture being zero or greater than zero, and the second numerical aperture being greater than the first numerical aperture.

7. The image processing method according to claim 5, wherein the processor acquires the information representing the interference light by obtaining the signal light from the optical system with the first numerical aperture and the optical system with the second numerical aperture, the optical system with the first numerical aperture illuminating the light from the light source onto the illuminated side object with parallel light flux, and the second numerical aperture being a numerical aperture that is set in advance.

8. The image processing method according to claim 6, wherein the processor acquires the information representing the interference light by obtaining the signal light from an optical system including the optical system with the first numerical aperture, the first numerical aperture being a numerical aperture NA conforming to a condition $0 \leq NA \leq 0.2$.

9. The image processing method according to claim 1, further comprising generating information for a display screen that displays the information projected into three-dimensional space as images.

10. An image processing device comprising memory and a processor, the processor being configured to:

acquire information representing interference light that is obtained by illuminating light from a light source through an optical system with a first numerical aperture onto an illuminated side object, transmitting signal light returning from the illuminated side object in response to the illuminated light through an optical system with a second numerical aperture, dividing a reference light from the light from the light source, and detecting the interference light between the signal light and the reference light; and perform processing including:

a first process of projecting the information representing the interference light onto a four-dimensional frequency aperture formed by the optical system with the first numerical aperture and the optical system with the second numerical aperture in a four-dimensional space of frequencies of the light source and frequencies of light in three dimensions representing the illuminated side object, and a second process of projecting the information projected by the first process into three-dimensional space.

11. An ophthalmological device, comprising:

a detection unit that detects interference light between signal light that is obtained by illuminating light from a light source at an eye to be examined and reference light that is divided from the light from the light source;

an illumination optical system formed with a first numerical aperture so as to illuminate the light from the light source onto the eye to be examined;

a detection optical system formed with a second numerical aperture so as to transmit light returning from the eye to be examined in response to the light illuminated through the illumination optical system, the detection optical system transmitting the returning light to the detection unit as the signal light, and the second numerical aperture being different from the first numerical aperture;

a processing section that performs processing based on information representing the interference light detected by the detection unit, the processing including:

a first process of projecting the information representing the interference light onto a four-dimensional frequency aperture formed by the optical system with the first numerical aperture and the optical system with the second numerical aperture in a four-dimensional space of frequencies of the light source and frequencies of light in three dimensions representing the eye to be examined, and a second process of projecting the information projected by the first process into three-dimensional space; and an image generation section that, based on the information processed by the processing section, generates a plurality of images corresponding to a plurality of planes at different depths in an optical axis direction.

12. A non-transitory storage medium storing a program for causing a computer to execute processing comprising:

acquiring information representing interference light that is obtained by illuminating light from a light source through an optical system with a first numerical aperture onto an illuminated side object, transmitting signal light returning from the illuminated side object in response to the illuminated light through an optical system with a second numerical aperture, dividing a reference light from the light from the light source, and detecting the interference light between the signal light and the reference light; and performing processing including:

a first process of projecting the information representing the interference light onto a four-dimensional frequency aperture formed by the optical system with the first numerical aperture and the optical system with the second numerical aperture in a four-dimensional space of frequencies of the light source and frequencies of light in three dimensions representing the illuminated side object, and a second process of projecting the information projected by the first process into three-dimensional space.

* * * * *